United States Patent
Hoeffner et al.

(10) Patent No.: US 12,168,761 B2
(45) Date of Patent: Dec. 17, 2024

(54) AUXILIARY MANIFOLD FOR A BIOREACTOR

(71) Applicant: Ark Biotech Inc., Westwood, MA (US)

(72) Inventors: Kai Hoeffner, Medway, MA (US); Zheng Huang, Bolton, MA (US); Savitha Panikar, Lowell, MA (US); Orianna Elysse Kane, Boston, MA (US); Zachary Allen Corriveau, Worcester, MA (US); William Fabrizio, Enfield, CT (US)

(73) Assignee: Ark Biotech Inc., Westwood, MA (US)

( * ) Notice: Subject to any disclaimer, the term of this patent is extended or adjusted under 35 U.S.C. 154(b) by 0 days.

(21) Appl. No.: 18/140,827

(22) Filed: Apr. 28, 2023

(65) Prior Publication Data

US 2023/0383227 A1   Nov. 30, 2023

Related U.S. Application Data

(60) Provisional application No. 63/345,270, filed on May 24, 2022.

(51) Int. Cl.
*C12M 1/00* (2006.01)
*C12M 1/36* (2006.01)

(52) U.S. Cl.
CPC ............ *C12M 23/40* (2013.01); *C12M 23/34* (2013.01); *C12M 29/04* (2013.01); *C12M 41/48* (2013.01)

(58) Field of Classification Search
CPC ...... C12M 29/04; C12M 23/34; C12M 23/40; C12M 41/48
See application file for complete search history.

(56) References Cited

U.S. PATENT DOCUMENTS

| | | | | |
|---|---|---|---|---|
| 4,833,089 | A | * | 5/1989 | Kojima .................. C12M 41/32 435/286.6 |
| 2009/0241698 | A1 | | 10/2009 | Biksacky |
| 2011/0201100 | A1 | * | 8/2011 | Proulx .................. C12M 23/44 435/287.1 |
| 2016/0025601 | A1 | | 1/2016 | Newbold |
| 2019/0203165 | A1 | * | 7/2019 | Wang ..................... C12M 23/58 |
| 2021/0340486 | A1 | * | 11/2021 | Andrews ............... C12M 23/44 |
| 2022/0042942 | A1 | | 2/2022 | Hoeffner |

OTHER PUBLICATIONS

Author Unknown, Automated Sampling Systems, Optimalbiotech.com, 2023.
Author Unknown, Maven Glucose & Lactate Analyzer, 908devices.com, 2023.
Author Unknown, Mobius® SensorReady Technology A Flexible Approach for Monitoring Mobius® Single-Use Bioreactors, MilliporeSigma, May 2017.
Author Unknown, Retractable Housings, hamiltoncompany.com, 2023.

* cited by examiner

*Primary Examiner* — Lydia Edwards
(74) *Attorney, Agent, or Firm* — Van Pelt, Yi & James LLP (57) ABSTRACT

A sample is introduced from a bioreactor to a chamber included in a manifold. The chamber includes at least a first probe. The at least the first probe is coupled to a controller. One or more measurements are performed on the sample while the sample is located in the chamber for a measurement period. The sample is returned from the chamber to the bioreactor after the one or more measurements of the sample have been performed.

16 Claims, 8 Drawing Sheets

AUXILIARY MANIFOLD FOR A BIOREACTOR

CROSS REFERENCE TO OTHER APPLICATIONS

This application claims priority to U.S. Provisional Patent Application No. 63/345,270 entitled BIOREACTOR HAVING AN AUXILIARY MANIFOLD filed May 24, 2022 which is incorporated herein by reference for all purposes.

BACKGROUND OF THE INVENTION

Bioreactors are used to grow cell culture. Most manufacturing processes typically involve collecting a sample of the raw ingredient(s), intermediate material and the final product from the bioreactor for the purpose of assessing their quality. The quality of the sampled material is often indicative of the progression of the process and also serves to check if the material meets the desired specifications.

The collection of a sample, i.e., sampling, especially from intermediate material, can be invasive to the process stream-material flow. Collecting a sample from the bioreactor during the process may break the aseptic boundary. Due to this, sampling is conducted via a preset sequence of steps to minimize process alteration and stoppage, material property alteration, and simultaneously, when applicable, prevent contamination, and breakage of sterile conditions. Depending on the manufacturing process and purpose of sample collection, material may be sampled at varying intervals during the process.

A bioreactor includes one or several probes that are located within the vessel of the bioreactor and are in direct contact with the bulk material. The probe outputs an inline reading that indicates a value associated with the bulk material. One problem with bioreactor probes is that they may fail during a manufacturing process. Material may be periodically sampled (e.g., daily) from the bioreactor to determine whether a bioreactor probe has failed. The material is sampled by removing a portion of the material from the bioreactor and using an offline instrument to test the sampled material. The offline instrument provides a reading (e.g., pH, dissolved $CO_2$, concentration). The offline reading associated with the sampled material is compared to an inline reading associated with the bulk material that is performed by a bioreactor probe. The offline reading may differ from the inline reading by a threshold amount. As a result, the bioreactor probe may need to be recalibrated or replaced to provide accurate readings. The same issue also applies to fermenters to some degree.

The inability to accurately monitor the bulk material as cells are growing within the bioreactor may cause a batch of the final product to fail because the final product does not meet the desired specifications. In some instances, the manufacturing process is terminated prior to the final product being created due to a probe that has substantially drifted. The probe needs to be physically removed from the bioreactor, replaced with a new probe, and the new probe needs to be calibrated before a new batch can start again. This causes extra costs to be incurred and reduces the throughput associated with the manufacturing process.

BRIEF DESCRIPTION OF THE DRAWINGS

Various embodiments of the invention are disclosed in the following detailed description and the accompanying drawings.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A technique to sterilely perform inline measurements of a bulk material included in a vessel is disclosed. The vessel may be a bioreactor or a fermenter. The disclosed technique utilizes an auxiliary manifold that is attached to a port associated with the vessel. The auxiliary manifold includes at least a controller, a tube, one or more sample chambers, and one or more probes in the one or more sample chambers.

The auxiliary manifold enables a portion of the bulk material to be collected and measured without breaking the aseptic boundary associated with the manufacturing process. The manifold mechanism overseeing the isolation of a portion of bioreactor or fermenter material (e.g., a liquid) to form the sample exerts stress that is smaller in magnitude than that experienced by liquids within most bioreactors or fermenters. Due to this, the operation of the auxiliary manifold causes minimal impact on the cell culture. Any stress accumulated from repeated cycling of liquid is still considerably smaller than that experienced due to the effects of mixing the liquid. This becomes especially true as the size of the vessel increases.

The auxiliary manifold includes a first valve that is situated between the sterile filter and the exhaust line. The auxiliary manifold includes a second valve situated between the pressurized gas source and the sterile filter. The first valve and the second valve are both initially in a closed state. The controller may send a control signal to the first valve that causes the first valve to change from a closed state to an open state. Subsequently, a portion of the bulk liquid is moved from the vessel and introduced into the first chamber forced by the pressure difference between the bioreactor and the first chamber. A quantity of the bulk liquid that is sufficient to submerge the probe(s) associated with the first chamber is introduced into the chamber. The controller may send a control signal to the first value that causes the first valve to change from open to closed. The first chamber includes at least a first probe. Measurements of the bulk liquid portion may be performed by the first probe for a predetermined amount of time (e.g., three minutes).

Subsequently, the bulk liquid portion is returned from the first chamber to the vessel. The controller may send a control signal to the second valve that causes the second valve to change from the closed state back to the open state. The sterile filter (e.g., gas filter) is situated between the first chamber and the gas input. The gas input provides a gas that is sterilized by the sterile filter. The sterilized gas has an associated pressure that causes the bulk liquid portion to be re-introduced into the vessel. After the bulk liquid portion has been re-introduced into the vessel, the controller may send a control signal to the second valve that causes the second valve to return back to its initial closed state. The second valve may remain open to allow for continuous flow of sterile gas into the vessel. Pressure regulators on the manifold control the flow rate of the bulk liquid while filing and emptying the first chamber in such a way that the liquid movement does not cause stress to the cells.

When a vessel associated with a bioreactor or fermenter is made, the number of ports available, the number of probes, and the types of probes that may be used are fixed. A complete redesign of the vessel associated with the bioreactor or fermenter may need to be performed to add an additional probe. The number of ports available, the number of ports, and the types of probes that may be used are different for vessels of different sizes and shapes. The disclosed auxiliary manifold is agnostic to the size and shape of the vessel, which provides flexibility in its applicability.

Figure 1:
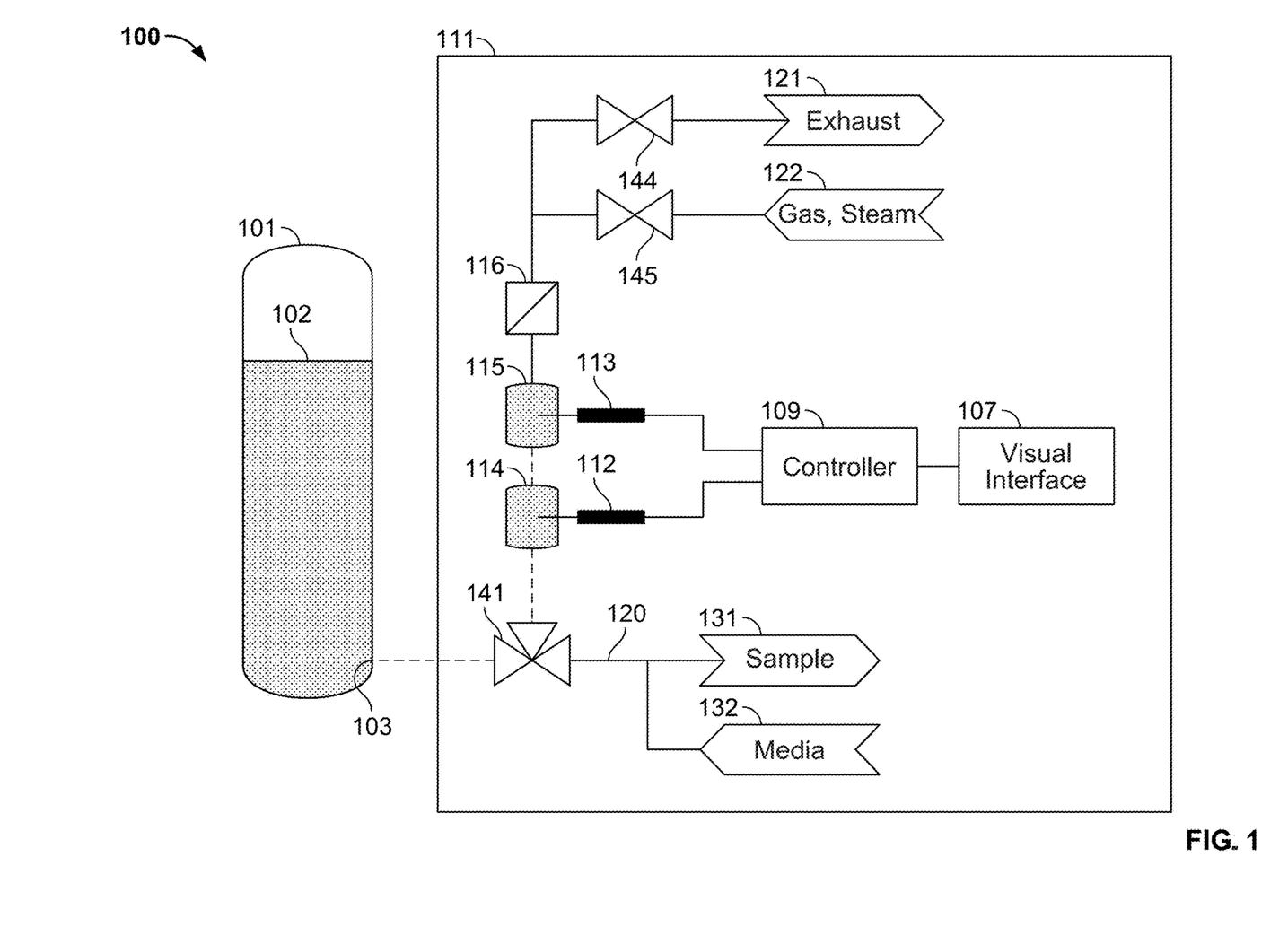
FIG. 1 is a block diagram illustrating a system for performing inline measurements of a bulk material in accordance with some embodiments.

FIG. 1 is a block diagram illustrating a system for performing inline measurements of bulk material in accordance with some embodiments. In the example shown, system 100 includes vessel 101 attached to manifold 111 via port 103. In some embodiments, vessel 101 is a bioreactor. In some embodiments, vessel 101 is a fermenter. Vessel 101 includes bulk material 102. Manifold 111 may be connected and disconnected to vessel 101 in a sterile manner before and during a bioreactor/fermenter operation, resulting in no compromise to the bioreactor/fermenter process, the cell growth, and/or the probe operation.

Manifold 111 includes chamber 114 and chamber 115. Chamber 114 and chamber 115 are stacked vertically. Although manifold 111 includes chambers 114, 115, manifold 111 may include 1:n chambers. Each chamber may include one or more probes. The size of a chamber can be varied for different designs to contain samples of varying amounts; the key being that the sample drawn by manifold 111, at any point, is small enough to not affect the mixing dynamics of the bulk liquid 102 remaining in vessel 101. The chamber size is of particular importance to small vessels (5L or less of working volume), the sample drawn should be substantial for the probes to perform their measurement yet small enough to not impact the mixing within vessel 101. In addition to the sample size, the frequency of sampling is also adjustable so as to be a balance between how update-to-date the measurement of vessel 101 is needed versus the constant change in liquid quantities in vessel 101.

Probe 112 is included in chamber 114 and probe 113 is included in chamber 115. A probe is inserted into a chamber perpendicular to the chamber or at an angle to suit the operation of the probe that requires an incline. If a single chamber houses multiple probes, the probes are stacked serially but spaced apart for a vertical or horizontal chamber. The probes can also be co-housed in a circular manner within a vertical chamber, the design of which extracts an even smaller quantity of liquid from the bioreactor. If the calibrants for one probe are incompatible with another probe, the probes housed in a common chamber are further isolated from each other by the use of valves to route the flow of the liquid.

Probes 112, 113 are connected to controller 109. Controller 109 is configured to automate the operation of manifold 111, inclusive of the initialization, calibration, measurement, and shutdown phases. Controller 109 allows for manifold 111 to work as a standalone device, independent of vessel 101, or be integrable with the automation system of vessel 101 to function in tandem.

Controller 109 is linked to storage (e.g., a historian, database, etc.) to save the quality and parametric data. Controller 109 functions in a dynamic manner: it reacts to changes in the measured values by adapting its responses accordingly. For example, in a closed loop control, at the start of the bioreactor/fermenter process, the hold times within manifold 111 are longer and as the process progresses the hold times shorten to reduce the time the bulk material sample is isolated from the bulk material 102.

Controller 109 is connected to visual interface 107. Visual interface 107 allows for ease of operation of manifold 111 and visualization of the relevant sample quality and manifold parametric values, tailored for non-subject matter experts. Data trending in real-time allows for the visualization of sensor and parametric data. Visual interface 107 may provide one or more measurement readings associated with probes 113, 114 during a measurement period in which the bulk material sample is stored in chambers 114, 115, respectively.

Manifold 111 includes valves 141, 144, and 145. Valves 144, 145 have a default state of closed. Valve 141 is a three-way valve. In some embodiments, controller 109 provides a control signal to valve 141 that changes the state of valve 141 such that a sample of the bulk liquid 102 may be extracted from vessel 101 and introduced into the tubing associated with manifold 111. A pressure difference between vessel 101 and manifold 111 may prevent the bulk liquid 102 from being introduced into chamber 114 and/or chamber 115. Controller 109 is configured to provide a control signal to valve 144 that causes valve 144 to change from a closed state to an open state. Subsequently, a sample of the bulk liquid 102 is moved from vessel 101 and introduced into chamber 114 forced by the pressure difference between vessel 101 and chamber 114. Gravity may assist in preventing the bulk liquid sample from being introduced into chamber 115. In some embodiments, a sample of the bulk liquid 102 is moved from vessel 101 and introduced into chamber 114 and chamber 115 forced by the pressure difference between vessel 101 and chambers 114, 115.

The sample of the bulk liquid 102 may be introduced to chamber 114 or both chambers 114, 115. In some embodiments, controller 109 provides a control signal to valve 141 that changes the state of valves 141, 144 such that a sample of the bulk liquid 102 is extracted from vessel 101 and introduced into chamber 114 or chambers 114, 115 Manifold 111 includes exhaust 121 (e.g., manifold vent), which enables the gas to be removed from manifold 111 and cause a pressure differential between vessel 101 and the chambers 114, 115.

Controller 109 may send a control signal to valve 144 that causes valve 144 to change from an open state to a closed state after a sufficient quantity of the bulk liquid sample has been introduced to chamber 114, chamber 115, or both. The contents of chambers 114, 115 may come in contact with other. Probes 112, 113 are configured to output a measurement associated with the bulk liquid sample during a measurement period. The measurement period corresponds to the duration in which the bulk liquid sample is included in a chamber.

After the measurement associated with the bulk liquid sample has been completed, the bulk liquid sample may be reintroduced back into vessel 101. Controller 109 is configured to provide a control signal to valve 145 that causes valve 145 to change from a closed state to an open state. A sterile filter 116 is situated between chamber 115 and valves 144, 145. Gas 122 (e.g., air, nitrogen, oxygen, carbon dioxide) may be introduced to manifold 111. Gas is sterilized via sterile filter 116. Gas 122 has an associated pressure that causes the bulk liquid sample to be re-introduced into vessel 101. The movement of the bulk liquid sample between manifold 111 and vessel 101 occurs in a smooth, steady manner (non-pulsed) thereby exerting only small magnitude forces, causing minimal to no stress on the cells. After the bulk liquid sample has been re-introduced into vessel 101, controller 109 may send a control signal to valve 145 that causes valve 145 to change from the open state back to the closed state.

In some embodiments, after the measurement associated with the bulk liquid sample has been completed, the bulk liquid sample may be diverted to sample port 131. Controller 109 may provide a control signal to valve 141 that change the state of valve 141 such that a sample of the bulk liquid 102 is extracted from vessel 101 and diverted to sample port 131.

The components of manifold 111 are designed and fitted in a way to ensure manifold 111 can be sterilized easily and maintains its sterility throughout the course of its use, especially by ensuring the absence of leaks. The connection between chamber 114 and chamber 115 may be broken without compromising sterility by either sterile welding or a combination of valves that allow for stem to sterilize the flow path. The connection between 103 and 141 may be broken without compromising sterility by either sterile welding or a combination of valves that allow for steam to sterilize the flow path. The design can be single-use using pre-manufactured parts and irradiated or assembled on site and autoclaved, or built and integrated with the clean in place (CIP) or steam in place (SIP) loops of a manufacturing facility.

Manifold 111 includes a SIP input 122. This enables parts of manifold 111 that come in contact with the bulk material sample along with the components housed within manifold 111 to be cleaned and sterilized. Manifold 111 may be cleaned while still being attached and during operation of vessel 101.

Controller 109 may perform a SIP by providing corresponding control signals to valves 141, 145 that causes valve 145 to change from a closed state to an open state and causes the state of valve 141 to be such that the flow path to port 120 is open. The SIP may be performed by inputting steam 122 into manifold 111. The steam may be removed from manifold 111 after the SIP has been completed. Controller 109 is configured to provide a control signal to valve 145 that causes valve 145 to change from an open state to a closed state. Subsequently, controller 109 is configured to provide a control signal to valve 144 to change valve 144 from a closed state to an open state, which causes the steam to be removed from manifold 111 via exhaust line 121. After the steam has been removed from manifold 111, controller 109 is configured to provide a control signal to valve 145 to change valve 145 from the open state to the closed state.

A probe may be calibrated/recalibrated before, during, or after operation of a bioreactor or fermenter. A probe that becomes non-functional during operation of a bioreactor or fermenter may be replaced from manifold 111 sterilely, without interruption to the bioreactor or fermenter process. Other systems may calibrate a probe within a bioreactor or a fermenter, and depending on the size of the bioreactor or fermenter, and placement of probes within, one might need to introduce large quantities of calibrant standards. In contrast, probes 112, 113 may be calibrated using fractional quantities of calibrant standards when compared to the probes of other systems. Furthermore, following the replacement of a faulty probe, calibrating the new sterile probe in the manifold is less tedious than calibrating the probe in a bioreactor or fermenter filled with material, with a process in progress.

In some embodiments, a probe is calibrated/recalibrated according to a schedule (e.g., daily, weekly, etc.). In some embodiments, a probe is calibrated/recalibrated based on criteria that indicates performance degradation of the probe (e.g., drift more than the drift threshold). In some embodiments, probes 112, 113 are calibrated using the same calibrant standard. A calibrant standard (e.g., media having a particular pH, dissolved oxygen, carbon dioxide) may be introduced into manifold 111 via port 120. Port 120 is sterilized prior to the calibrant standard being introduced. The calibrant standard may be introduced into chamber 114 or chamber 115, depending on which of the probes 112, 113 are being calibrated. An amount of calibrant standard being introduced into a chamber is of quantity sufficient to submerge the probe(s) being calibrated.

In some embodiments, probes 112, 113 are calibrated using a different calibrant standard. The configuration of chambers 114, 115 enables probes 112, 113 to be isolated from each other where there is an incompatibility in calibrant standards such that probe 112 is not calibrated using the calibrant standard for probe 113 and vice versa.

In some embodiments, controller 109 provides a control signal to valve 141 that changes the state of valve 141 such that the calibrant standard is introduced into chamber 114. In some embodiments, controller 109 provides a control signal to valve 141 that changes the state of valve 141 such that calibrant standard is introduced into chamber 115 and chamber 114. In some embodiments, the calibrant standard is drained via port 120. In some embodiments, the calibrant standard is introduced into vessel 101. After a probe is calibrated, sterile water may be introduced via port 120 into the chamber that includes the calibrated probe to rinse the calibrated probe and drained via port 120.

In some embodiments, a bulk material sample 131 is removed from manifold 111 via port 120 for additional testing. In some embodiments, out-of-specification material is diverted and drained from vessel 101 to waste via port 120. In some embodiments, media 132 is introduced into vessel 101 via port 120 to replenish vessel 101. In some embodiments, controller 109 provides a control signal to valve 141 that changes the state of valve 141 to allow media 132 to be introduced into vessel 101.

After manifold 111 has completed its tasks for vessel 101, it may be detached from vessel 101 by disconnecting the sterile tubing from port 103.

Figure 2:
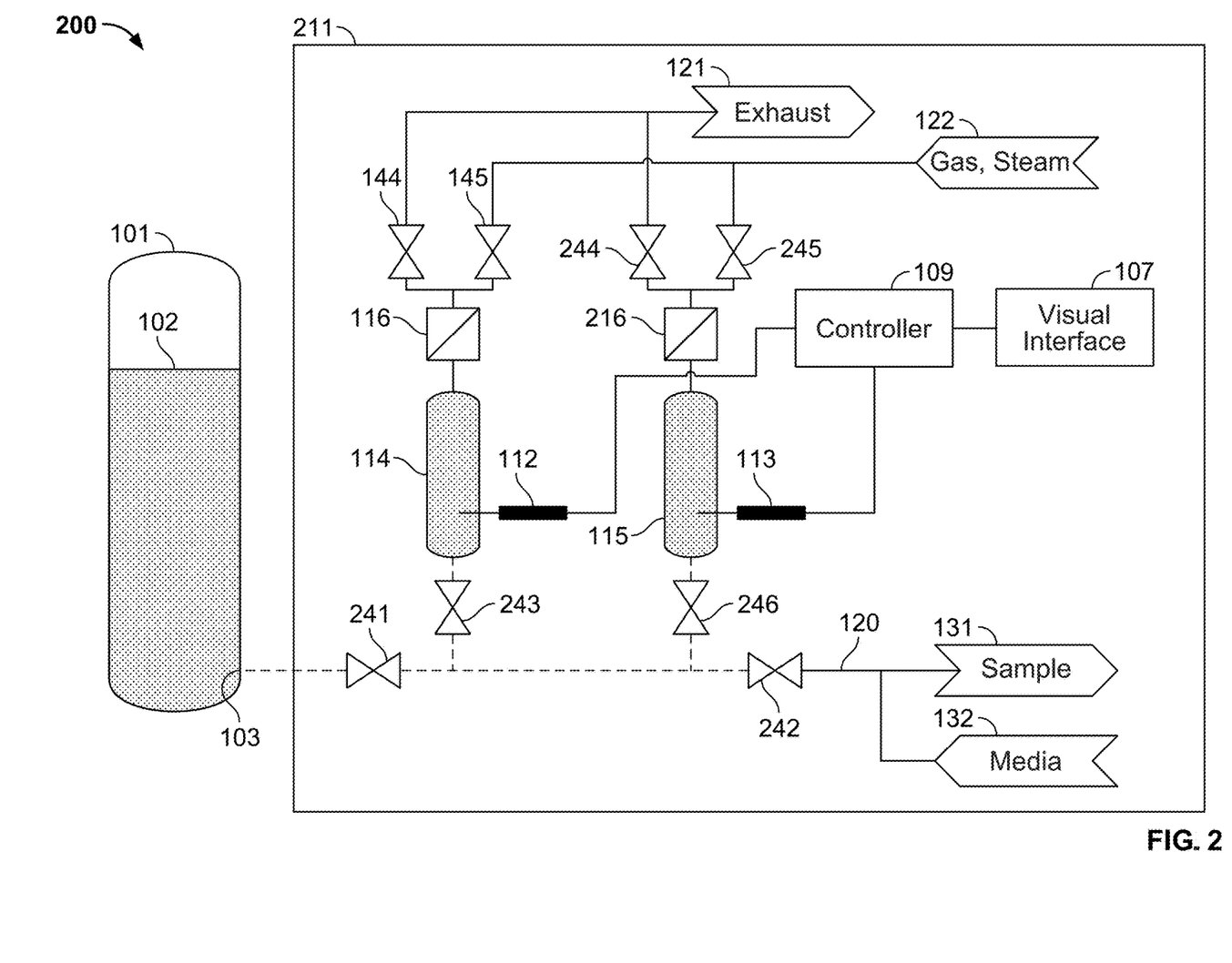
FIG. 2 is a block diagram illustrating a system for performing inline measurements of a bulk material in accordance with some embodiments.

FIG. 2 is a block diagram illustrating a system for performing inline measurements of a bulk material in accordance with some embodiments. In the example shown, system 200 includes vessel 101 attached to manifold 211 via port 103. Manifold 211 is similar to manifold 111, except that manifold 611 includes two-way valves 241, 242, 243, 244, 245, 246, and sterile filter 216. Valves 241, 242, 243, 244, 245, 246 together with valves 144, 145 allow for the dedicated filling and emptying chambers 114, 115 and measuring and calibration of their respective probes 112, 113. Valves 241, 242, 243, 244, 245, 246 have a default state of a closed state.

In some embodiments, a sample of the bulk liquid 102 is introduced into chamber 114 and not introduced into chamber 115. In some embodiments, a sample of the bulk liquid 102 is introduced into chamber 115 and not introduced into chamber 114. For example, one of the probes in a first chamber may need to be replaced, but measurements of the bulk liquid sample may be performed using the remaining probe(s) in a second chamber. In some embodiments, a sample of the bulk liquid 102 is introduced into chambers 114, 115.

To introduce a sample of the bulk liquid 102 into chamber 114, controller 109 provides a control signal to valve 241 that changes the state of valve 241 such that a sample of the bulk liquid 102 may be extracted from vessel 101 and introduced into the tubing associated with manifold 211. Controller 109 provides corresponding control signals to valves 243, 144 to change the corresponding states of valves 243, 144 from a closed state to an open state. Subsequently, a sample of the bulk liquid 102 is moved from vessel 101 and introduced into chamber 114 forced by the pressure difference between the vessel 101 and chamber 114. Controller 109 may send a control signal to valve 144 that causes valve 144 to change from an open state to a closed state after a sufficient quantity of the bulk liquid sample has been introduced to chamber 114. Probe 112 is configured to output a measurement associated with the bulk liquid sample during a measurement period. After the measurement associated with the bulk liquid sample has been completed, the bulk liquid sample may be reintroduced back into vessel 101. Controller 109 is configured to provide a control signal to valve 145 that causes valve 145 to change from a closed state to an open state. A sterile filter 116 is situated between chamber 114 and valves 144, 145. Gas 122 (e.g., air, nitrogen, oxygen, carbon dioxide) may be introduced to manifold 111. Gas is sterilized via sterile filter 116. Gas 122 has an associated pressure that causes the bulk liquid sample to be re-introduced into vessel 101.

To introduce a sample of the bulk liquid 102 into chamber 115, controller 109 provides a control signal to valve 241 that changes the state of valve 241 such that a sample of the bulk liquid 102 may be extracted from vessel 101 and introduced into the tubing associated with manifold 211. Controller 109 provides corresponding control signals to valves 246, 244 to change the corresponding states of valves 246, 244 from a closed state to an open state. Subsequently, a sample of the bulk liquid 102 is moved from vessel 101 and introduced into chamber 114 forced by the pressure difference between the vessel 101 and chamber 115. Controller 109 may send a control signal to valve 244 that causes valve 244 to change from an open state to a closed state after a sufficient quantity of the bulk liquid sample has been introduced to chamber 115. Probe 113 is configured to output a measurement associated with the bulk liquid sample during a measurement period. After the measurement associated with the bulk liquid sample has been completed, the bulk liquid sample may be reintroduced back into vessel 101. Controller 109 is configured to provide a control signal to valve 245 that causes valve 245 to change from a closed state to an open state. A sterile filter 216 is situated between chamber 115 and valves 244, 245. Gas 122 (e.g., air, nitrogen, oxygen, carbon dioxide) may be introduced to manifold 211. Gas is sterilized via sterile filter 216. Gas 122 has an associated pressure that causes the bulk liquid sample to be re-introduced into vessel 101.

Probes 112, 113 of manifold 211 may be calibrated in a similar manner as probes 112, 113 of manifold 111. In some embodiments, controller 109 provides a control signal to valves 242, 243 that changes the state of valves 242, 243 such that the calibrant standard is introduced into chamber 114. In some embodiments, controller 109 provides a control signal to valves 242, 246 that changes the state of valve 242, 246 such that the calibrant standard is introduced into chamber 115. In some embodiments, controller 109 provides a control signal to valves 242, 243, 246 that changes the state of valve 242, 243, 246 such that the calibrant standard is introduced into chamber 114 and chamber 115. In some embodiments, the calibrant standard is drained via port 120. In some embodiments, the calibrant standard is introduced into vessel 101. After a probe is calibrated, sterile water may be introduced via port 120 into the chamber that includes the calibrated probe to rinse the calibrated probe and drained via port 120.

Figure 3:
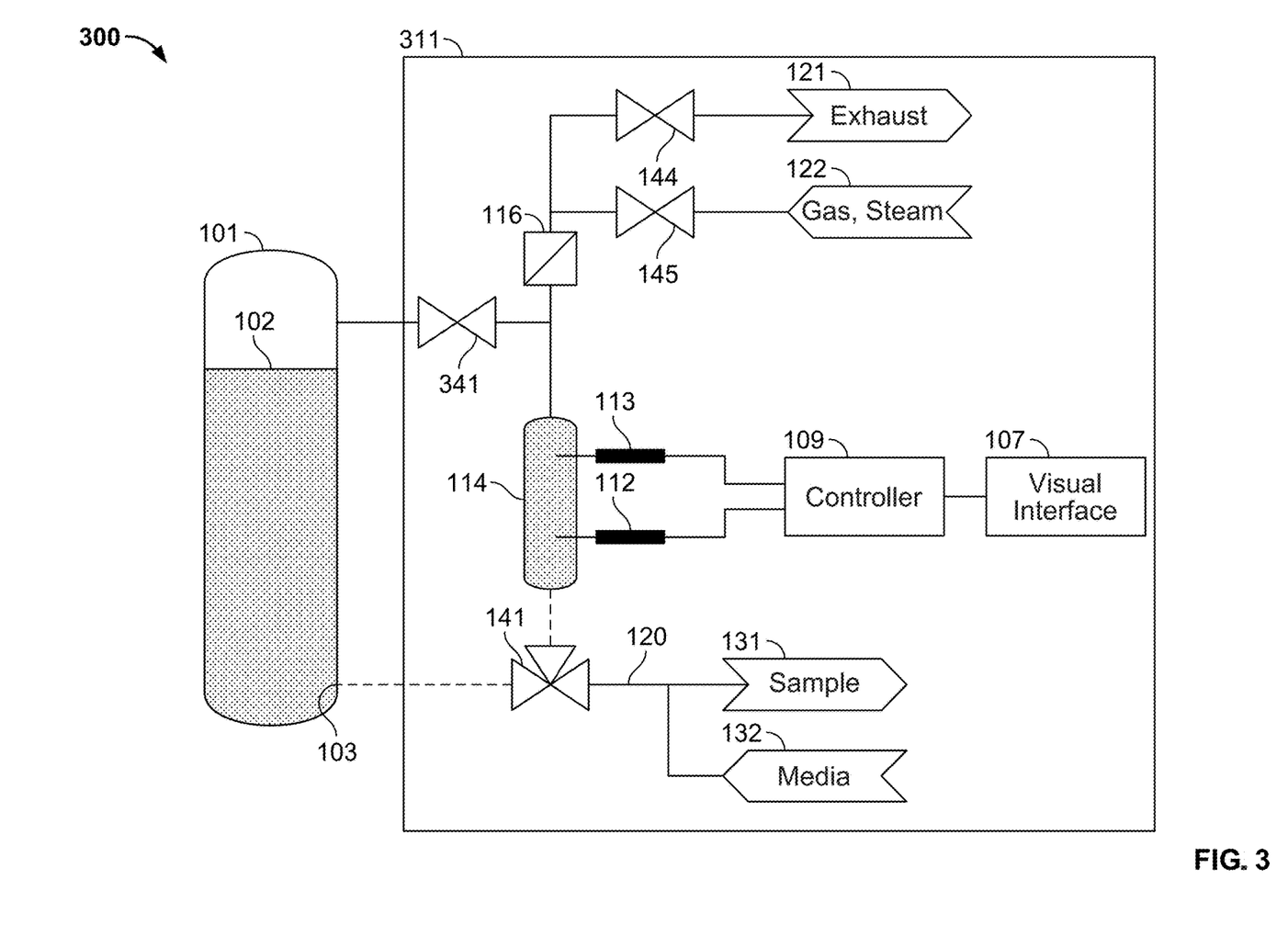
FIG. 3 is a block diagram illustrating a system for performing inline measurements of a bulk material in accordance with some embodiments.

FIG. 3 is a block diagram illustrating a system for performing inline measurements of a bulk material in accordance with some embodiments. In the example shown, system 300 includes vessel 101 attached to manifold 311 via port 103. Manifold 311 is similar to manifold 111, except that manifold 311 includes valve 341. In some embodiments, the auxiliary manifold is connected the vessel headspace through a valve 341. When both valves between vessel 101 and auxiliary manifold 311 are opened, auxiliary manifold 311 is automatically filled to the same liquid level as the bioreactor. No liquid level control is required.

Figure 4:
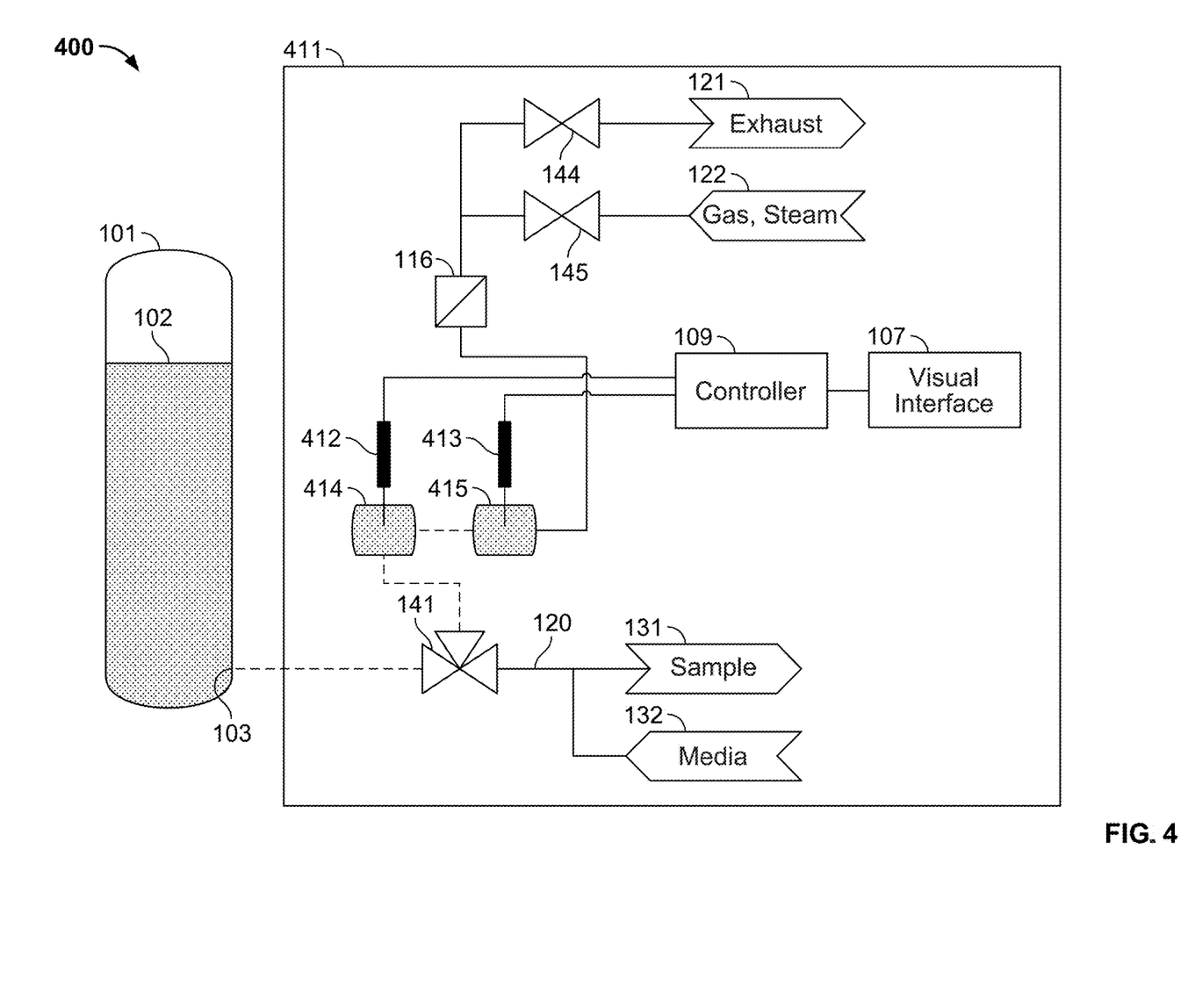
FIG. 4 is a block diagram illustrating a system for performing inline measurements of a bulk material in accordance with some embodiments.

FIG. 4 is a block diagram illustrating a system for performing inline measurements of a bulk material in accordance with some embodiments. In the example shown, system 400 includes vessel 101 attached to manifold 411 via port 103. Manifold 411 is similar to manifold 111 except that chambers 414, 415 are stacked horizontally instead of being stacked vertically. Manifold 411 operates in a manner similar to manifold 111. Although manifold 411 includes chambers 414, 415, manifold 411 may include 1:n chambers.

Each chamber may include one or more probes. Probe 413 is included in chamber 415 and probe 412 is included in chamber 412. Probes 412, 413 are connected to controller 109. Controller 109 is connected to visual interface 107. Visual interface 107 may provide one or more measurement readings associated with probes 412, 413.

Figure 5:
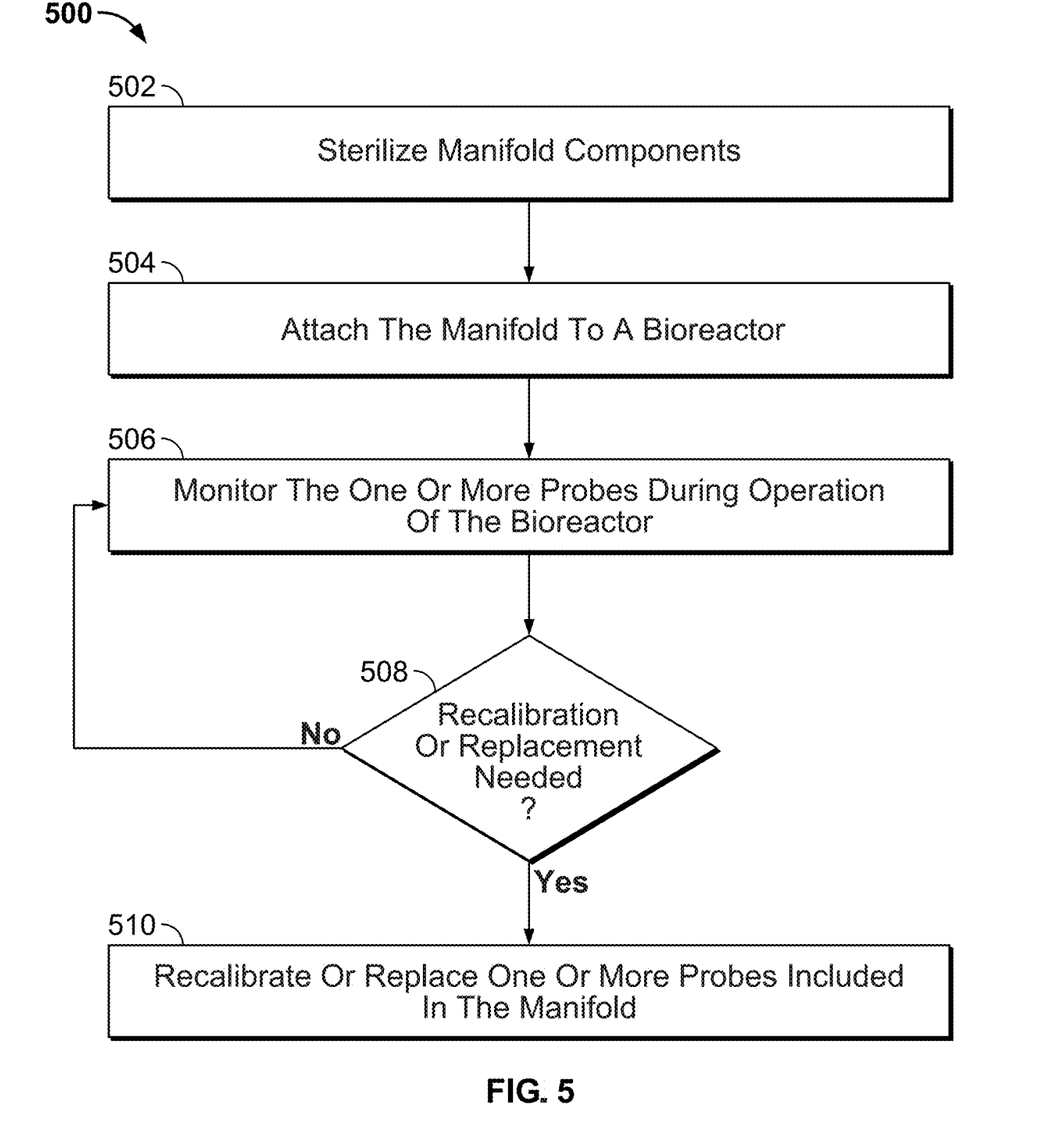
FIG. 5 is a flow diagram illustrating a process for implementing an auxiliary manifold in accordance with some embodiments.

FIG. 5 is a flow diagram illustrating a process for implementing an auxiliary manifold in accordance with some embodiments.

At 502, the manifold components are sterilized. The manifold components may be sterilized using steam or another sterilization agent.

At 504, the manifold is attached to a bioreactor. The manifold may be coupled to the bioreactor via sterilely welded tubing. The manifold may be coupled to the bioreactor/fermenter via steam-in-place connections. The sterilized manifold may be welded on at any point prior to or during the bioreactor operation. The sterilized probe(s) are calibrated within the manifold ahead of time and kept ready before the manifold is welded to the bioreactor. If the probes require an additional product calibration, this is performed following the welding to the bioreactor and initiating liquid movement.

At 506, one or more probes included in the manifold are monitored during operation of the bioreactor. The manifold may include one or more chambers. Each chamber includes one or more probes. Each of the probes is connected to a controller. The controller is linked to storage (e.g., a historian, database, etc.) to save the quality and parametric data associated with the one or more probes. The controller is connected to a visual interface, which provides a visualization of the relevant sample quality and manifold parametric values, tailored for non-subject matter experts. Data trending in real-time allows for the visualization of sensor and parametric data.

During a measurement period, i.e., when a bulk material sample is included in the chamber(s) of the manifold, the one or more probes included in the manifold are expected to output an expected value. The measured values associated with the one or more probes are compared to the expected values associated with the one or more probes.

The manifold may include different types of probes (e.g., pH, dissolved oxygen (DO), partial pressure of carbon dioxide ($pCO_2$), capacitance, etc.). The measured value of a first type of probe may be compared to the expected value for the first type of probe, the measured value of a second type of probe may be compared to the expected value for the second type of probe, ..., and the measured value for an nth type of probe may be compared to the expected value for the nth type of probe.

In some embodiments, the comparison indicates that the probe needs to be calibrated. For example, the probe measurement may exceed the expected value by a threshold value. In some embodiments, the comparison indicates that the probe needs to be replaced. For example, the probe may not be providing any measurement to the controller.

At 508, it is determined whether any of the one or more probes need to be recalibrated or replaced.

In response to a determination that none of the one or more probes need to be replaced, process 500 returns to step 506. The one or more probes associated with the manifold may be monitored until the bioreactor process has completed. In some embodiments, the one or more probes are monitored according to a schedule (e.g., daily, weekly, etc.). In response to a determination that at least one of the probes needs to be recalibrated or replaced, process 500 proceeds to step 510.

At 510, one or more probes included in the manifold are recalibrated or replaced. In some embodiments, the one or more probes having a measured value that exceed the expected value by a threshold amount are recalibrated. A probe may be recalibrated by introducing a calibrant standard via a port into the chamber in which the probe is located. The calibrant standard is specific to the type of measurement performed by the probe. The calibrant standard may be drained from the manifold after the probe has been recalibrated.

In some embodiments, the one or more probes that do not prove a measured value are replaced. If a probe needs to be swapped mid-operation, either the entire manifold can be switched by severing the tubing sterilely or only the chamber containing the probe in question. This may be performed without compromising the current bioreactor run.

Figure 6:
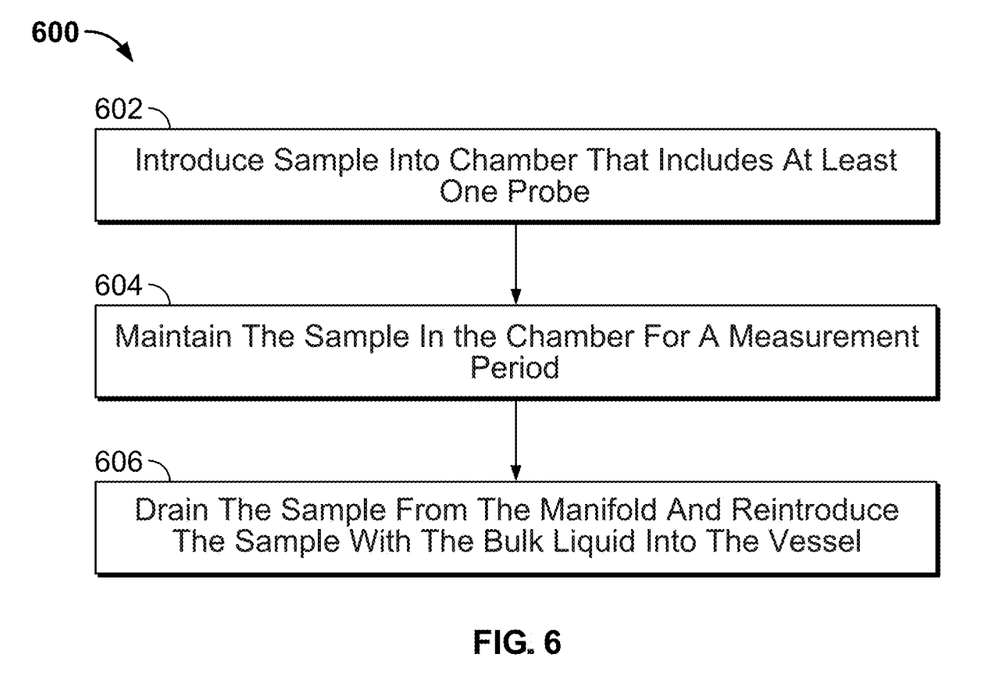
FIG. 6 is a flow diagram illustrating a process for operating an auxiliary manifold in accordance with some embodiments.

FIG. 6 is a flow diagram illustrating a process for operating an auxiliary manifold in accordance with some embodiments. In the example shown, process 600 may be implemented by a controller, such as controller 109. In some embodiments, process 600 is implemented to perform some or all of step 506 of process 500.

At 602, a sample is introduced into a chamber that includes at least one probe. The auxiliary manifold enables a portion of the bulk material to be collected without breaking the aseptic boundary associated with the manufacturing process. The auxiliary manifold includes a valve situated between the sterile filter and the exhaust. A controller provides a control signal to the valve that causes the valve to change from a closed state to an open state. Subsequently, a sample of the bulk liquid is transferred from the vessel and introduced into the chamber. The controller provides a control signal to the valve that causes the valve to change from the open state back to the closed state.

At 604, the sample is maintained in the chamber for a measurement period. One or more measurements are performed during the measurement period. In some embodiments, the one or more measurements include specific and total oxygen update rate (OUR). In some embodiments, the one or more measurements include specific and total carbon evolution rate (CER). In some embodiments, the one or more measurements include buffer capacity of the media in the sample. In some embodiments, the one or more measurements include specific uptake rates of nutrients (e.g., glucose, glutamine, lactate, etc.). In some embodiments, the one or more measurements include specific production rate of metabolites (e.g., lactate, ammonia, etc.).

At 606, the sample is drained from the manifold and reintroduced into the bulk liquid of the vessel. The sterile filter (e.g., gas filter) is situated between the second valve and a gas input. The controller provides a control signal to the second valve that causes the second valve to change from a closed state to an open state. The gas input provides a gas that is sterilized by the sterile filter. The sterilized gas has an associated pressure that causes the bulk liquid portion to be re-introduced into the vessel. Pressure regulators on the manifold control the flow rate of the bulk liquid while filling and emptying the chamber in such a way that the liquid movement does not cause stress to the cells.

Figure 7:
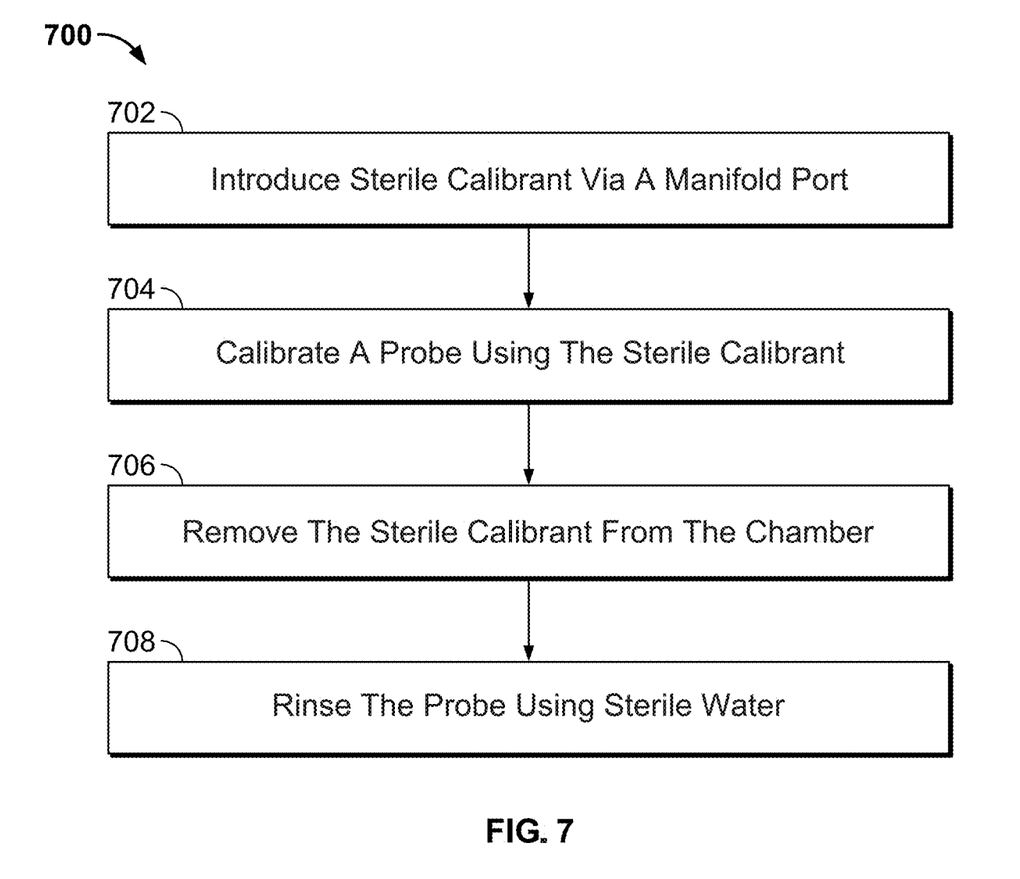
FIG. 7 is a flow diagram illustrating a process for calibrating a probe in accordance with some embodiments.

FIG. 7 is a flow diagram illustrating a process for calibrating a probe in accordance with some embodiments. In the example shown, process 700 may be implemented by an auxiliary manifold, such as manifolds 111, 211, 311, 411.

At 702, a sterile calibrant is introduced into a chamber that includes a probe via a manifold port. A manifold may include a plurality of chambers, each chamber including one or more probes. The sterile calibrant is specific to a probe, such that the sterile calibrant introduced into a first chamber may be different from the sterile calibrant introduced into a second chamber.

At 704, the probe is calibrated using the sterile calibrant. A measurement of the probe with the sterile calibrant is performed and compared to the expected value of the sterile calibrant. Measurements associated with the probe are adjusted based on the comparison.

At 706, the sterile calibrant is removed from the chamber. In some embodiments, the sterile calibrant is removed from the chamber via a drain port. In some embodiments, the sterile calibrant is introduced into a vessel associated with a bioreactor or fermenter to reduce the risk of contaminating the manifold (e.g., a contamination risk exists when the sterile calibrant is removed from the manifold via the drain port).

At 708, the probe is rinsed using sterile water.

Figure 8:
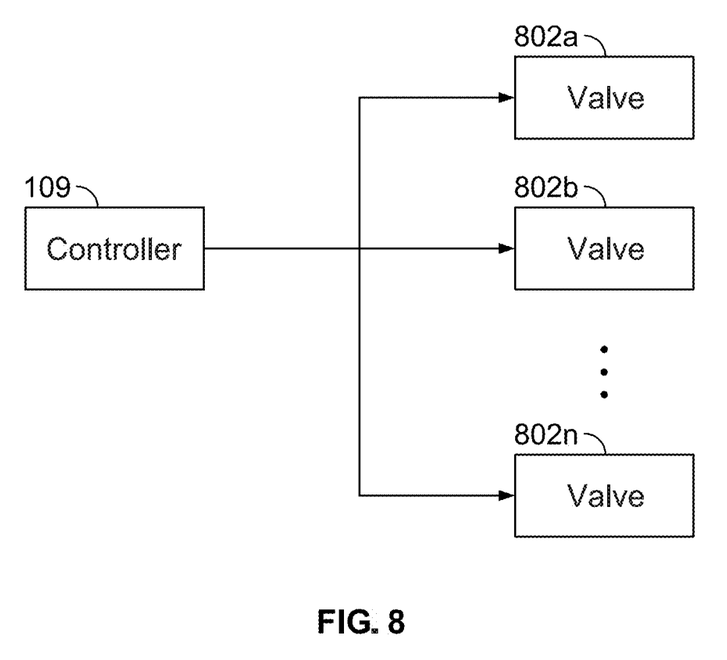
FIG. 8 is a block diagram illustrating a controller coupled to a plurality of valves in accordance with some embodiments.

FIG. 8 is a block diagram illustrating a controller coupled to a plurality of valves in accordance with some embodiments. In the example shown, controller 109 is coupled to valves 802*a*, 802*b*, . . . , 802*n*. Although FIG. 8 depicts controller 109 being coupled to three valves, controller 109 may be coupled to n valves. In some embodiments, a valve is a two-way valve. In some embodiments, a valve is a three-way valve. A valve of FIG. 8 may correspond to valves 141, 144, 145, 241, 242, 243, 244, 245, 341. Controller 109 is configured to provide a control signal to any of the valves 802*a*, 802*b*, . . . , 802*n*. In some embodiments, the control signal causes a valve to change from a closed state to an open state. In some embodiments, the control signal causes a valve to change from an open state to a closed state.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A manifold, comprising:
   a controller;
   a tube;
   a sample chamber to temporarily store a sample of bulk material stored in a cell culture vessel growing cell culture;
   a first valve positioned in between a sterile filter and an exhaust, wherein the sterile filter is positioned in between the sample chamber and the first valve;
   a second valve positioned in between the sterile filter and a gas inlet, wherein the sterile filter is located in between the sample chamber and the second valve; and
   at least a first probe included in the sample chamber, wherein the at least the first probe, the first valve, and the second valve are coupled to the controller,
   wherein the at least the first probe is configured to measure a corresponding value associated with the sample of the bulk material provided from the cell culture vessel to the sample chamber via the tube, wherein the manifold is attached to a port associated with the cell culture vessel via the tube.

2. The manifold of claim 1, wherein the sample is a liquid.

3. The manifold of claim 1, wherein the cell culture vessel is a bioreactor.

4. The manifold of claim 1, wherein the cell culture vessel is a fermenter.

5. The manifold of claim 1, wherein the sample chamber includes the first probe and one or more other probes.

6. The manifold of claim 5, wherein the first probe and the one or more other probes are stacked serially.

7. The manifold of claim 1, wherein the sample chamber is a horizontal chamber.

8. The manifold of claim 1, wherein the sample chamber is a vertical chamber.

9. The manifold of claim 1, further comprising a second sample chamber and a second probe, wherein the second probe is included in the second sample chamber.

10. The manifold of claim 1, wherein a default state associated with the first valve and the second valve is a closed state.

11. The manifold of claim 10, wherein the controller is configured to provide a first control signal to the first valve to change from the closed state to an open state, wherein the sample is provided from the cell culture vessel to the sample chamber after a state of the first valve changes from the closed state to the open state.

12. The manifold of claim 11, wherein the controller is configured to provide a second control signal to the first valve to change from the open state to the closed state after a sufficient amount of the sample has been introduced into the sample chamber.

13. The manifold of claim 12, wherein the controller is configured to perform one or more measurements on the sample while the sample is located in the sample chamber for a measurement period.

14. The manifold of claim 13, wherein the one or more measurements include at least one of a specific and total oxygen update rate, specific and total carbon evolution rate, buffer capacity of media in the sample, specific uptake rates of nutrients, and/or specific production rate of metabolites.

15. The manifold of claim 13, wherein the controller is configured to provide a third control signal to the second valve to change from the closed state to the open state, wherein a gas input is filtered by the sterile filter, wherein the gas input has an associated pressure that causes the sample to return from the sample chamber back into the cell culture vessel.

16. The manifold of claim 1, further comprising a calibration port, wherein a calibrant standard is provided to the sample chamber to calibrate the at least the first probe via the calibration port.

\* \* \* \* \*